United States Patent
Forthmann et al.

(10) Patent No.: US 8,483,443 B2
(45) Date of Patent: Jul. 9, 2013

(54) METHOD FOR CHARACTERIZING OBJECT MOVEMENT FROM CT IMAGING DATA

(75) Inventors: Peter Forthmann, Sandesneben (DE); Holger Schmitt, Hamburg (DE); Udo van Stevendaal, Ahrensburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 194 days.

(21) Appl. No.: 13/124,289

(22) PCT Filed: Oct. 6, 2009

(86) PCT No.: PCT/IB2009/054371
§ 371 (c)(1),
(2), (4) Date: Apr. 14, 2011

(87) PCT Pub. No.: WO2010/046797
PCT Pub. Date: Apr. 29, 2010

(65) Prior Publication Data
US 2011/0200232 A1   Aug. 18, 2011

Related U.S. Application Data

(60) Provisional application No. 61/107,685, filed on Oct. 23, 2008.

(51) Int. Cl.
*G06K 9/00* (2006.01)
(52) U.S. Cl.
USPC .......................... 382/107; 600/512; 600/509
(58) Field of Classification Search
USPC .................. 382/100, 107, 131, 132
See application file for complete search history.

(56) References Cited

U.S. PATENT DOCUMENTS

| | | | | |
|---|---|---|---|---|
| 6,098,561 | A * | 8/2000 | Forthmann | 114/144 C |
| 7,266,408 | B2 * | 9/2007 | Bojovic et al. | 600/512 |
| 7,269,516 | B2 * | 9/2007 | Brunner et al. | 702/19 |
| 7,580,798 | B2 * | 8/2009 | Brunner et al. | 702/19 |
| 7,751,875 | B2 * | 7/2010 | Bojovic et al. | 600/512 |
| 7,882,135 | B2 * | 2/2011 | Brunner et al. | 707/791 |
| 7,971,429 | B2 * | 7/2011 | Forthmann et al. | 60/295 |
| 7,992,376 | B2 * | 8/2011 | Forthmann et al. | 60/286 |
| 8,059,787 | B2 * | 11/2011 | Forthmann et al. | 378/156 |
| 8,209,002 | B2 * | 6/2012 | Vajdic et al. | 600/512 |
| 8,300,765 | B2 * | 10/2012 | Gotman et al. | 378/62 |
| 8,311,618 | B2 * | 11/2012 | Vajdic et al. | 600/512 |
| 2003/0004652 | A1 * | 1/2003 | Brunner et al. | 702/19 |
| 2003/0083822 | A2 * | 5/2003 | Brunner et al. | 702/19 |

(Continued)

FOREIGN PATENT DOCUMENTS

| WO | 2007072281 A2 | 6/2007 |
|---|---|---|
| WO | 2008050334 A2 | 5/2008 |

OTHER PUBLICATIONS

Point Tracked Quantitative Analysis of LEft Ventricular Motion from 3D Image Sequences, Pengcheng Shi, Yale Univ. 2000.*

(Continued)

*Primary Examiner* — Jayesh A Patel
*Assistant Examiner* — Iman K Kholdebarin

(57) ABSTRACT

A method is provided for using CT imaging data to characterize the movement of a moving object. The method calculates one or more motion values based on motion vectors which are representative of the object's movement. The moving object may be, for example, a beating heart.

22 Claims, 3 Drawing Sheets

U.S. PATENT DOCUMENTS

| | | | |
|---|---|---|---|
| 2003/0158483 A1 | 8/2003 | Jackson et al. | |
| 2005/0209525 A1* | 9/2005 | Bojovic et al. | 600/512 |
| 2006/0083416 A1 | 4/2006 | Nishiura | |
| 2007/0014452 A1 | 1/2007 | Suresh et al. | |
| 2007/0268993 A1* | 11/2007 | Forthmann et al. | 378/4 |
| 2008/0205722 A1 | 8/2008 | Schaefer et al. | |
| 2008/0306980 A1* | 12/2008 | Brunner et al. | 707/102 |
| 2009/0238328 A1* | 9/2009 | Forthmann et al. | 378/14 |
| 2009/0310737 A1* | 12/2009 | Forthmann et al. | 378/8 |
| 2010/0179446 A1* | 7/2010 | Bojovic et al. | 600/512 |
| 2011/0002444 A1* | 1/2011 | Schmitt et al. | 378/62 |
| 2011/0044559 A1* | 2/2011 | Erhard et al. | 382/275 |
| 2011/0095197 A1* | 4/2011 | Forthmann et al. | 250/393 |
| 2011/0200232 A1* | 8/2011 | Forthmann et al. | 382/107 |

OTHER PUBLICATIONS

Pointed—Tracked Quantitative analysis, Pengcheng Shi, 2000, Yale Univ. Department of Electricial Engineering p. 1-50.*

Point Tracked Quantitative Analysis of Left Ventricular Motion from 3D Image sequences, Pengcheng Shi, Albert J Sinusas, Oct. 2000, Yale Univ.*

Fan, L., et al.; LV motion estimation based on the integration of continuum mechanics and estimation theory; 1999; Proc. SPIE—The International Soc. For Optical Engineering; v. 3660; Abstract.

A. Frangi, W. Niessen, M. Viergever, "Three-Dimensional Modeling for Functional Analysis of Cardiac Images: A Review", IEEE Transactions on Medical Imaging, vol. 20, No. 1, (2001).

E. Heiberg, "Automated Feature Detection in Multidimensional Images", Linkoping University, Department of Biomedical Engineering, (2004).

M.I. Sa, "Imaging Techniques in Cardiac Resynchronization Therapy", Int. J. Cardiovasc. Imaging, vol. 24, No. 1, pp. 89-105 (2007).

Shi, P., et al.; Point-Tracked Quantitative Analysis of Left Ventricular Surface Motion from 3-D Image Sequences; 2000; IEEE Trans. on Medical Imaging; 19(1)36-50.

M. Suhling, "Myocardial Motion and Deformation Analysis from Echocardiograms", (2004) 182 pages.

* cited by examiner

METHOD FOR CHARACTERIZING OBJECT MOVEMENT FROM CT IMAGING DATA

CROSS REFERENCE TO RELATED APPLICATIONS

This application claims the benefit of U.S. provisional application Ser. No. 61/107,685 filed Oct. 23, 2008, which is incorporated herein by reference.

The present application relates generally to the imaging arts and more particularly to a method and apparatus for computed tomography (CT) based cardiac imaging. It has application at least in such cardiac imaging, and will be described with particular reference thereto. However, it may also find more general application in other kinds of imaging, especially wherever a moving object is being imaged, and in other arts.

CT imaging may be used to generate a 4D volume reconstruction of a patient's heart or other organ(s). By "4D" it is meant that multiple three dimensional images are reconstructed, each representing the configuration of the organ(s) at different points in time over a time period. Thus the time period is the fourth dimension. When placed in chronological order, the 3D volume reconstructions show the timing and amplitude of the organ movement over the time period. For example, in cardiac imaging, the timing and amplitude of the heart's pumping motion, and the relation between contractions of the various cardiac chambers, can be shown by a 4D volume reconstruction. Physicians can use such reconstructions to diagnose and treat a patient. For example, 4D cardiac reconstructions may be used in diagnosing cardiac dysfunction, or programming an implanted device to regulate the beating of the heart, or planning and implementing surgical procedures in or around the heart, and the like.

According to one aspect of the present invention, a method is provided for using CT imaging data to characterize the movement of a moving object such as a beating heart. While the method finds particular use in connection with cardiac imaging, it more generally finds application in imaging any other moving object. It may also find application in other kinds of imaging, different from CT.

One advantage resides in obtaining useful functional information regarding internal organs from a CT imaging scan. Numerous additional advantages and benefits will become apparent to those of ordinary skill in the art upon reading the following detailed description of preferred embodiments.

The invention may take form in various components and arrangements of components, and in various process operations and arrangements of process operations. The drawings are only for the purpose of illustrating preferred embodiments and are not to be construed as limiting the invention.

Figure 1:
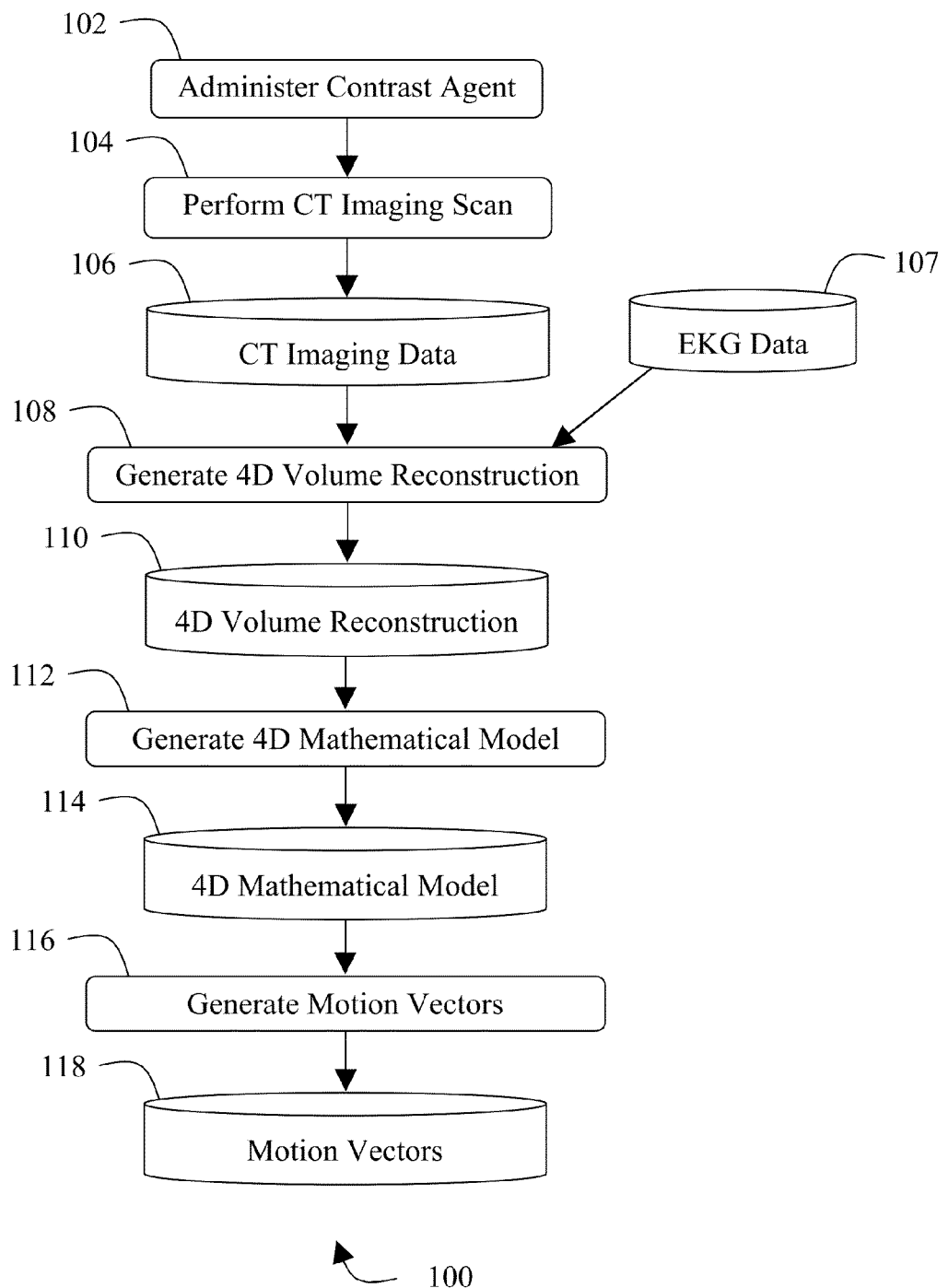
FIG. 1 illustrates an exemplary process 100 for characterizing the movement of an object over a period of time.

The method and apparatus described here are directed generally to any CT-based imaging process to produce images showing movement of a moving object. An exemplary such process 100 is illustrated in FIG. 1. In the representative example of cardiac imaging the organs being imaged principally include the heart and perhaps related blood vessels. In other applications, other organs might be imaged, such as other blood vessels, lungs, stomach, kidneys, brain, liver, bones, and the like. The illustrative process 100 can be adapted to suit such applications.

In order to obtain useful CT images, a contrast agent may first be administered 102 into areas of interest within the patient's body. The contrast agent functions to make particular regions or structures more detectable by x-rays than they would be without the contrast agent. In cardiac imaging, this may be accomplished for example by using a needle to inject the contrast agent into a vein in a patient's arm and waiting for a suitable amount of contrast agent to reach the heart and coronary vein(s). It may alternatively be accomplished by inserting a catheter into the coronary vein(s) and releasing the contrast agent directly into the blood stream there, which is a more invasive and difficult procedure than injection by needle into the arm.

Once the regions or structures to be imaged have been prepared for detection by a CT scan, if desired or needed, then a CT imaging scan is performed 104 to generate CT imaging data 106. Such CT scans 104 are usually performed while the patient is holding his or her breath. Of course, for cardiac imaging, the patient's heart is beating during the scan. The CT imaging data 106 comprises a series of projected x-ray images. The projections may be electronically processed to produce one or more three dimensional CT images, using conventional processes. Such three dimensional images can be displayed and manipulated on a standard two-dimensional display device such as a computer monitor.

The CT imaging data 106 is used to generate 108 a 4D volume reconstruction 110 of the region(s) or structure(s) of interest. The 4D volume reconstruction 110 may be a series of low resolution three dimensional images, to reduce the required processing time and related data storage, but they may alternatively be high resolution images. The time-indexing of the three dimensional images may be accomplished by retrospectively gating the CT imaging scan 104.

Taking cardiac imaging as a representative example, retrospective gating may be accomplished by utilizing an electrocardiogram 107 to determine the heart's electrical activity over time. Matching the heart's electrical activity during the CT scan 104 against the EKG cycle 107 permits a time index to be generated, based on the patient's cardiac cycle. Other methods of retrospective gating may be employed. The time period of the 4D reconstruction 110 may be one complete cardiac cycle, or it may be shorter or longer. A sufficient number of three dimensional images are reconstructed to provide a good estimation of the overall organ movement during the time period. For an entire cardiac cycle, it is believed that approximately 40 to 60 such images are sufficient, and about 50 such images is preferred.

The 4D reconstruction 110 may be used to generate 112 a mathematical 4D model 114 of the imaged regions or structures of interest. The mathematical 4D model 114 approximates the movement of the organ(s) or other moving object(s) over a specified time period, such as one complete pumping cycle of the heart in cardiac imaging. Thus, according to such a mathematical 4D model 114, an imaged organ may be idealized by a series of surface mesh images. Each surface mesh image consists of several flat surfaces such as triangles which meet at vertices or nodes. The organ's shape and movement over the time period is then idealized by movement of the nodes, which in turn changes the shape of the flat surfaces, and thus the appearance of the surface mesh. The detail and accuracy of such models increases with the number of nodes utilized, and also with smaller time intervals interposed between successive surface mesh images.

Figure 2:
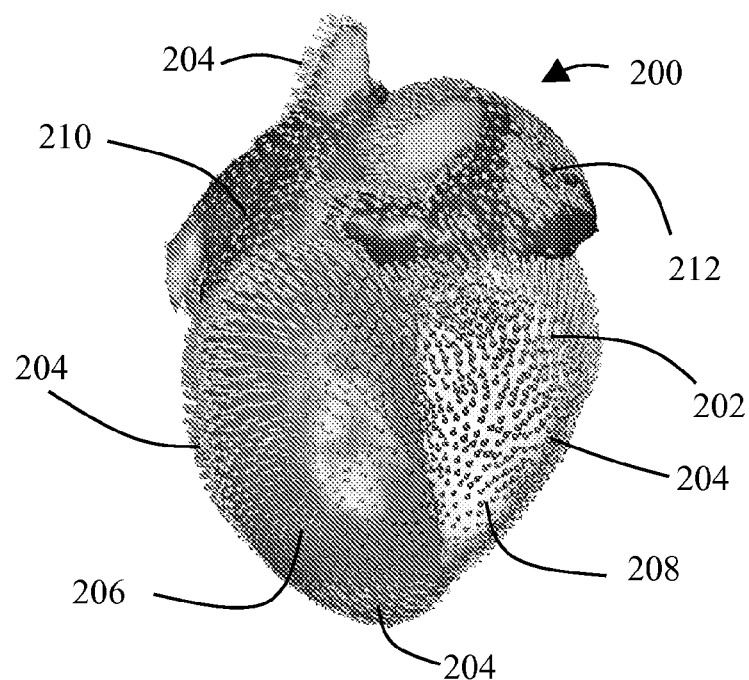
FIG. 2 is a representative surface mesh model of a patient's heart, including motion vectors.

The 4D mathematical model 114 may in turn be used to generate 116 a series of localized motion vectors 118 corresponding to various parts of the imaged organ or other moving object over the imaging time period. This may be done simultaneously or sequentially with the generation of the mathematical 4D model 114. Thus, in each successive surface mesh image of the mathematical 4D model 114 over the imaged time period, a localized motion vector may be assigned to each node. The localized motion vector reflects the magnitude and direction of the node's displacement or movement to its position in the next surface mesh image of the mathematical 4D model 114. Localized motion vectors may additionally or alternatively be assigned to the flat surfaces of the surface mash images. FIG. 2 shows a surface mesh image of 200 of a heart 202, with several motion vectors 204.

Figure 3:
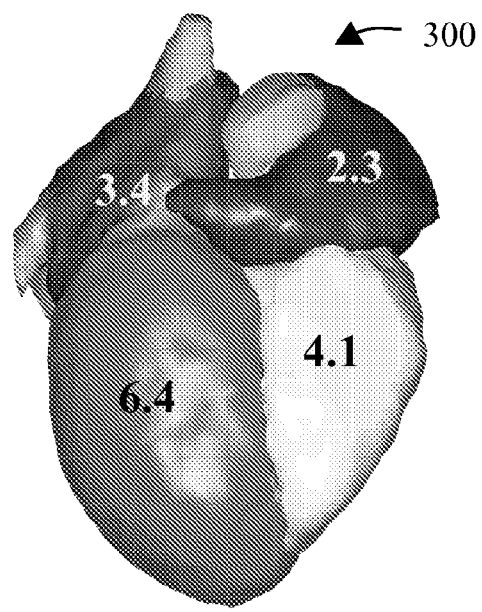
FIG. 3 is a representative surface mesh model of a patient's heart, showing the normalized sum of the absolute values of the motion vectors in FIG. 2.

The various motion vectors 204 may be used to characterize the movement of the organ or other moving object being imaged, or portions thereof, over time. Taking the surface mesh image 200 of FIG. 2 as a representative example, the movement of the right ventricle 206, left ventricle 208, right atrium 210 and left atrium 212 may be of particular interest to a treating physician in many situations. Such movement may be characterized in a number of ways using the motion vectors 204. For example, the normalized sum of the magnitudes of the motion vectors 204 respectively corresponding to each of the four heart chambers 206, 208, 210 and 212 may be calculated. In other words, for each region of interest, the magnitudes of the motion vectors 204 in that region are summed up to a total value, which is then divided by the surface area of the region. FIG. 3 shows the result of such a calculation for the motion vectors 204 in FIG. 2. Thus, the normalized sum of the magnitudes of the motion vectors, or motion value, corresponding to the right ventricle 206 is 6.4 cm, and so on as illustrated in FIG. 3. Similar motion value calculations can be made with respect to each surface mesh image in the mathematical 4D model 114, in relation to the next succeeding surface mesh image in time, to characterize the movement of the heart over the imaging time period.

Additional motion values different from or in addition to the normalized sum of vector magnitudes may be calculated. For example, one might merely record the maximum vector magnitude, or the minimum vector magnitude, or both, as a motion value in order to characterize the movement of the imaged object. As yet another alternative, the derivative of the motion vectors (i.e. an acceleration value) may be used as a motion value to characterize the movement of the imaged object. Various other motion value alternatives are available for using the motion vectors to characterize the movement of the imaged object, either on their own or in combination with other calculations.

In some cardiac imaging contexts, it may be advantageous to consider the movement of the heart as a whole, without differentiating between the four chambers. Thus a similar motion value calculation, determining the normalized sum of the magnitudes of the motion vectors across the entire heart, may be made to characterize the overall movement of the heart as a whole.

More generally, then, the function of imaged organ(s) or other moving object(s) may be characterized as a whole, or as portions of a whole, as the particular context requires. For example, a motion value calculation can be made for both lungs at once with one single motion value, or separately for the right and left lungs as two motion values, or further subdividing each lung into multiple portions of interest as several motion values.

The measured motion value or values of the imaged organ or other moving object can be used by a physician to understand the timing and magnitude of organ function over time. The measured motion values may be useful on their own, but they can be particularly useful in connection with other information. As one example, the measured motion values may be compared with benchmark motion values reflecting average, standard, or normal movement of the organ. Different benchmark values may be used as dependent upon the patient's gender, weight, age, or other characteristics which might affect organ movement. If the measured motion values are sufficiently close to the benchmark values, then that might suggest the organ is behaving normally or is otherwise in good health. Conversely, if the measured motion values are too far from the benchmark values, then that might suggest the organ is not behaving normally, or is in poor health.

As another example, the measured motion values may be compared with benchmark motion values reflecting poor, unhealthy, or abnormal functioning of the organ. In that case, if the measured motion values are sufficiently close to the benchmark values, then that might suggest the organ is not behaving normally, or is in poor health.

As yet another example, the measured motion values may be compared with previously measured motion values of the same organ in the same patient. In such situations, if the difference between the currently measured values and the previously measured values is large enough, then that might suggest something about the organ's operation has significantly changed (for the good, or the worse, depending on the nature of the change).

Figure 4:
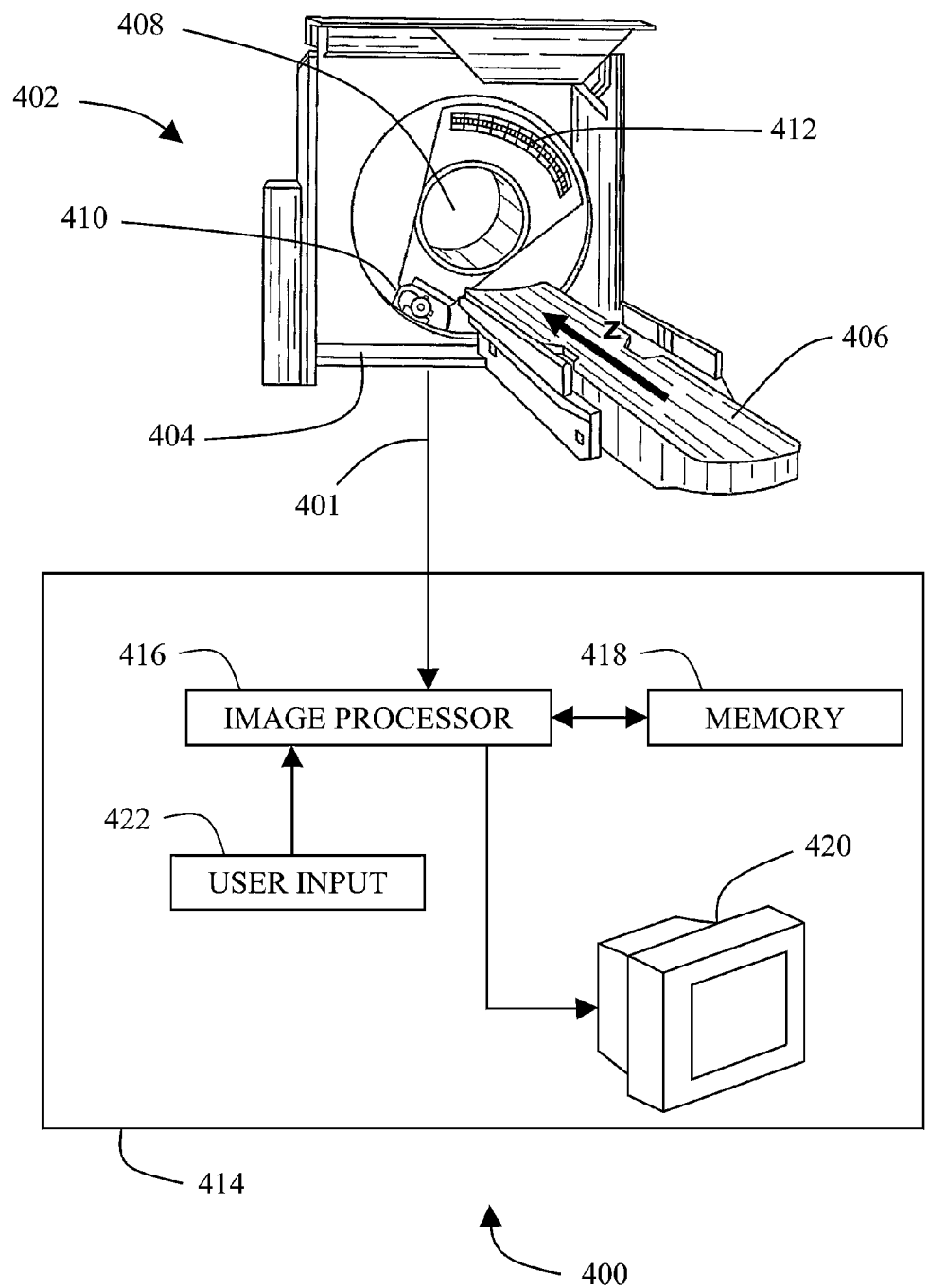
FIG. 4 illustrates a CT imaging apparatus.

FIG. 4 illustrates one example of a CT imaging apparatus 400 for carrying out the process 100 to characterize organ or other object movement. A CT imaging acquisition system 402 includes a gantry 404 and a table 406 which moves along the z-axis. A patient or other subject to be imaged (not shown) lies down on the table 406 and is moved to be disposed within an aperture 408 in the gantry 404. Once the patient is in position, an x-ray source 410 and an x-ray detector 412 rotate together around the aperture 408 to record the CT imaging data 106 described above.

The CT imaging acquisition system 402 then passes the CT imaging data 106 on to a CT imaging processing and display system 414 through a communication link 401. Although the systems 402 and 414 are shown and described here as being separate systems for purposes of illustration, they may in other embodiments be part of a single system. The CT imaging data 106 passes to an image processor 416 which stores the data 106 in a memory 418. The memory 418 may also store other data, such as for example EKG data 107 used in cardiac imaging. The image processor 416 electronically processes the data 106 to carry out the process 100 described above. The image processor 416 can show the resulting images on an associated display 420. A user input 422 such as a keyboard and/or mouse device may be provided for a user to control the processor 416.

Thus the aforementioned functions can be performed as software logic. "Logic," as used herein, includes but is not limited to hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), or other programmed logic device. Logic may also be fully embodied as software.

"Software," as used herein, includes but is not limited to one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory such as memory 418, part of an operating system or other type of executable instructions. It will be appreciated by one of ordinary skill in the art that the form of software is dependent on, for example, requirements of a desired application, the environment it runs on, and/or the desires of a designer/programmer or the like.

The systems and methods described herein can be implemented on a variety of platforms including, for example, networked control systems and stand-alone control systems. Additionally, the logic shown and described herein preferably resides in or on a computer readable medium such as the memory 418. Examples of different computer readable media include Flash Memory, Read-Only Memory (ROM), Random-Access Memory (RAM), programmable read-only memory (PROM), electrically programmable read-only memory (EPROM), electrically erasable programmable read-only memory (EEPROM), magnetic disk or tape, optically readable mediums including CD-ROM and DVD-ROM, and others. Still further, the processes and logic described herein can be merged into one large process flow or divided into many sub-process flows. The order in which the process flows herein have been described is not critical and can be rearranged while still accomplishing the same results. Indeed, the process flows described herein may be rearranged, consolidated, and/or re-organized in their implementation as warranted or desired.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof. The invention may take form in various components and arrangements of components, and in various steps and arrangements of steps. The drawings are only for purposes of illustrating the preferred embodiments and are not to be construed as limiting the invention.

The invention claimed is:

1. A method of imaging a moving object, the method comprising:
   obtaining imaging data relating to a moving object;
   using the imaging data to generate a mathematical 4D model of movement of at least a portion of the moving object between a first time and a second time;
   using the mathematical 4D model to calculate a plurality of different localized motion vectors, wherein each different motion vector identifies a movement of a different corresponding location on the portion of the moving object between the first time and the second time; and
   combining the plurality of motion vectors to calculate one or more measured motion values, wherein the one or more measured motion values characterize the movement of the portion of the moving object between the first time and the second time, by determining at least one of:
   (a) a normalized sum of the magnitudes of the motion vectors, wherein the normalized sum is a sum of the motion vectors of the portion of the moving object divided by a surface area of the portion; and
   (b) a derivative of the motion vectors.

2. The method of claim 1, further comprising using the imaging data to generate a 4D reconstruction of the moving object, and using the 4D reconstruction to generate the mathematical 4D model.

3. The method of claim 1, wherein the mathematical 4D model comprises multiple mathematical shapes representing the moving object, and each mathematical shape is defined by multiple flat surfaces which meet at nodes.

4. The method of claim 1, wherein the imaging data comprises CT imaging data.

5. The method of claim 1, wherein the measured motion values are compared against benchmark motion values to provide a comparative result.

6. The method of claim 5, wherein the benchmark motion values reflect average, standard, or normal movement of the moving object.

7. The method of claim 5, wherein the benchmark motion values reflect poor, unhealthy, or abnormal movement of the moving object.

8. The method of claim 5, wherein the benchmark motion values comprise previously measured motion values of the moving object.

9. The method of claim 5, wherein the benchmark motion values are determined at least in part by one or more of an imaged patient's gender, weight, or age.

10. The method of claim 1, wherein the moving object is a heart of a human or animal patient.

11. The method of claim 10, wherein measured motion values are separately calculated for each chamber of the heart.

12. An apparatus for imaging a subject having an internal organ, the apparatus comprising:
    an x-ray source and an x-ray detector to perform a CT imaging scan of the internal organ to generate CT imaging data; and
    a computer readable medium comprising logic to:
      use the CT imaging data to generate a mathematical 4D model of movement of at least a portion of the internal organ between a first time and a second time;
      use the mathematical 4D model to calculate a plurality of different localized motion vectors, wherein each different motion vector identifies a movement of a different corresponding location on the portion of the imaged organ between the first time and the second time; and
      combine the plurality of motion vectors to calculate one or more measured motion values, wherein the one or more measured motion values characterize the movement of the portion of the moving object between the first time and the second time, by determining at least one of:
      (a) a normalized sum of the magnitudes of the motion vectors, wherein the normalized sum is a sum of the motion vectors of the portion of the moving object divided by a surface area of the portion; and
      (b) a derivative of the motion vectors.

13. The apparatus of claim 12, further comprising logic to use the CT imaging data to generate a 4D reconstruction of the internal organ, and use the 4D reconstruction to generate the mathematical 4D model.

14. The apparatus of claim 12, wherein the mathematical 4D model comprises multiple mathematical shapes representing the imaged organ, and each mathematical shape is defined by multiple flat surfaces which meet at nodes.

15. The apparatus of claim 14, wherein the measured motion values are compared against benchmark motion values to provide a comparative result.

16. The apparatus of claim 15, wherein the benchmark motion values reflect average, standard, or normal movement of the internal organ.

17. The apparatus of claim 15, wherein the benchmark motion values reflect poor, unhealthy, or abnormal movement of the internal organ.

18. The apparatus of claim 15, wherein the benchmark motion values comprise previously measured motion values of the internal organ in the patient.

19. The apparatus of claim 15, wherein the benchmark motion values are determined at least in part by one or more of the imaged patient's gender, weight, or age.

20. The apparatus of claim 12, wherein the internal organ is a heart.

21. The apparatus of claim 20, wherein measured motion values are separately calculated for each chamber of the heart.

22. A method of imaging an internal organ, the method comprising:
  obtaining CT imaging data relating to the internal organ;
  using the CT imaging data to generate a 4D reconstruction of at least a portion of the internal organ;
  using the 4D reconstruction to generate a mathematical 4D model of movement of the internal organ between a first time and a second time; and
  using the mathematical 4D model to calculate a plurality of different localized motion vectors, wherein each different motion vector identifies a movement of a different corresponding location on the portion of the internal organ between the first time and the second time; and
  combining the plurality of motion vectors to calculate one or more measured motion values, wherein the one or more measured motion values characterize the movement of the portion of the moving object between the first time and the second time, by determining at least one of:
  (a) a normalized sum of the magnitudes of the motion vectors, wherein the normalized sum is a sum of the motion vectors of the portion of the moving object divided by a surface area of the portion; and
  (b) a derivative of the motion vectors.

* * * * *